(12) United States Patent
Sheinis (10) Patent No.: US 9,395,534 B2
(45) Date of Patent: Jul. 19, 2016

(54) OPTICAL SYSTEM FOR CORRECTION OF TISSUE INDUCED ABERRATION

(75) Inventor: Andrew Sheinis, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 2211 days.

(21) Appl. No.: 11/945,488

(22) Filed: Nov. 27, 2007

(65) Prior Publication Data

US 2009/0137990 A1 May 28, 2009

(51) Int. Cl.
| | |
|---|---|
| *A61F 9/008* | (2006.01) |
| *G02B 21/06* | (2006.01) |
| *G02B 26/06* | (2006.01) |
| *G02B 21/00* | (2006.01) |

(52) U.S. Cl.
CPC .............. *G02B 26/06* (2013.01); *A61F 9/008* (2013.01); *G02B 21/0072* (2013.01); *A61F 2009/00863* (2013.01)

(58) Field of Classification Search
CPC .......... A61F 9/008; A61F 2009/00863; G02B 21/0072; G02B 26/06
See application file for complete search history.

(56) References Cited

U.S. PATENT DOCUMENTS

| | | | | |
|---|---|---|---|---|
| 5,289,557 | A * | 2/1994 | Sheinis et al. | 292/336.3 |
| 5,815,233 | A * | 9/1998 | Morokawa et al. | 349/57 |
| 6,483,641 | B1 * | 11/2002 | MacAulay | 359/385 |
| 6,722,767 | B2 * | 4/2004 | Dick et al. | 351/211 |
| 2002/0008148 | A1 * | 1/2002 | Empedocles et al. | 235/494 |
| 2002/0057431 | A1 * | 5/2002 | Fateley et al. | 356/330 |
| 2003/0025874 | A1 * | 2/2003 | Williams et al. | 351/200 |
| 2004/0102765 | A1 * | 5/2004 | Koenig | 606/5 |
| 2004/0227932 | A1 * | 11/2004 | Yoon | 356/121 |
| 2006/0109534 | A1 * | 5/2006 | Grebinski | 359/15 |
| 2006/0244906 | A1 * | 11/2006 | Piers et al. | 351/161 |
| 2007/0046948 | A1 * | 3/2007 | Podoleanu et al. | 356/497 |
| 2007/0263226 | A1 * | 11/2007 | Kurtz et al. | 356/492 |

OTHER PUBLICATIONS

Ono, et al., Aspherical Mirror Testing Using a CGH with Small Errors, Applied Optics, vol. 24, No. 4, pp. 560-563, Feb. 15, 1985, Optical Society of America, Washington, DC, USA.

Gruneisen, et al., Diffractive Wavefront Control with Programmable Spatial Light Modulator Technology, Advanced Wavefront Control: Methods, Devices, and Applications IV, edited by Micahel K. Giles, et al., Proc. of SPIE vol. 6306, 630601 (2006), pp. 1-1-1-12, Bellingham, WA, USA.

Duncan, et al. DLP Switched Blaze Grating; the Heart of Optical Signal Processing, MOEMS and Miniaturized Systems III, James H. Smith, Editor, Proc. of SPIE vol. 4983 (2003), pp. 297-304, Bellingham, WA, USA.

(Continued)

*Primary Examiner* — David Shay
(74) *Attorney, Agent, or Firm* — Boyle Fredrickson, S.C.

(57) ABSTRACT

A multi-photon fluoroscopy microscope employs an electronically controlled diffraction mask to affect correcting phase adjustments in an incident waveform to allow a precise focus of the stimulating beam of light to a focal point within tissue having a varying and inhomogeneous index of refraction.

3 Claims, 5 Drawing Sheets

(56) References Cited

OTHER PUBLICATIONS

Gruneisen, et al., Near-Diffraction-Limited Compensated Imaging and Laser Wavefront Control with Programmable Diffractive Optics, High-Resolution Wavefront Control: Methods, Devices and Applications, IV, John D. Gonglewski, et al, Editors, Proc. of SPIE vol. 4825, (2002), pp. 147-157, Bellingham, WA, USA.

Lin et al., Optical Networking by DLP-based Switched-Blazed-Grating, Holography, Diffractive Optics, and Applications II, eited by Sheng, et al, Proc. of SPIE vol. 5636, (2005), pp. 48-55, Bellingham, WA, USA.

* cited by examiner

OPTICAL SYSTEM FOR CORRECTION OF TISSUE INDUCED ABERRATION

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

It is often desirable to image biological tissue through intervening tissues or structure, for example, through overlying light transmissive layers of cells (e.g., in the breast) or through fluids (e.g., the aqueous or vitreous humor in the eye). Imaging through intervening tissue or structure allows tissue to be studied in relatively thick sections or in vivo.

To a limited extent, such imaging of internal structures may be done using a conventional microscope by focusing the microscope objective "through" the overlying layers so that the structure of interest is at the focal plane of the microscope objective and sharply in focus and other overlying structures are defocused.

Confocal microscopy takes this process a step further by placing a light stop in the optical path to block all light not received from the single focal spot of the microscope objective. Scanning the focal spot through the tissue and measuring variations of brightness as a function of that scan, can produce an image free from light interference from adjacent layers in the tissue. Unfortunately, the optical stop significantly limits the light through the confocal microscope, requiring a bright light source usually provided by a laser and long exposure times.

Recently developed techniques allow virtually any protein in a cell to be tagged with fluorescent molecules. The fluorescent molecules, and thus the tagged cells, can then be visualized by exciting the fluorescent molecule with an excitation light beam. The excitation beam is typically of a different frequency than the frequency of fluorescence so that a dichroic filter can be used to block the excitation beam, making the tagged tissue stand out.

Figure 1:
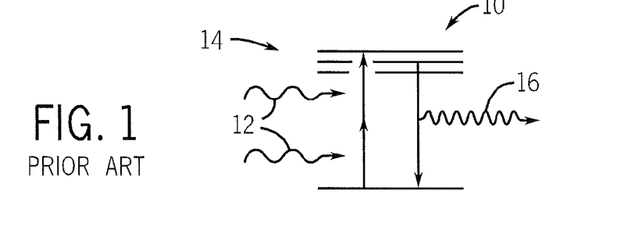
FIG. 1 is an electron energy diagram illustrating the principle of multi-photon fluorescence.

Referring to FIG. 1, an improved variation on confocal microscopy makes use of this fluorescent tagging in a process called multi-photon fluorescence. In multi-photon fluorescence, a fluorescent molecule 10 may simultaneously absorb two (or more) photons 12 to move to an excited state 14 elevated by at least twice the energy of each individual photon 12. A subsequently emitted fluorescence 16 will have approximately twice the frequency of the stimulating photons 12 to be readily distinguishable from the photons 12 of the exciting beam. Importantly, the property of multi-photon fluorescence is nonlinearly related to light intensity and thus multi-photon fluorescence can be controlled to occur in only small regions where the excitation light beam is focused to an intensity causing significant multi-photon fluorescence. Tissue before and after this focused region, even if tagged by the fluorescent molecules, will exhibit only weak multi-photon fluorescence.

Figure 2:
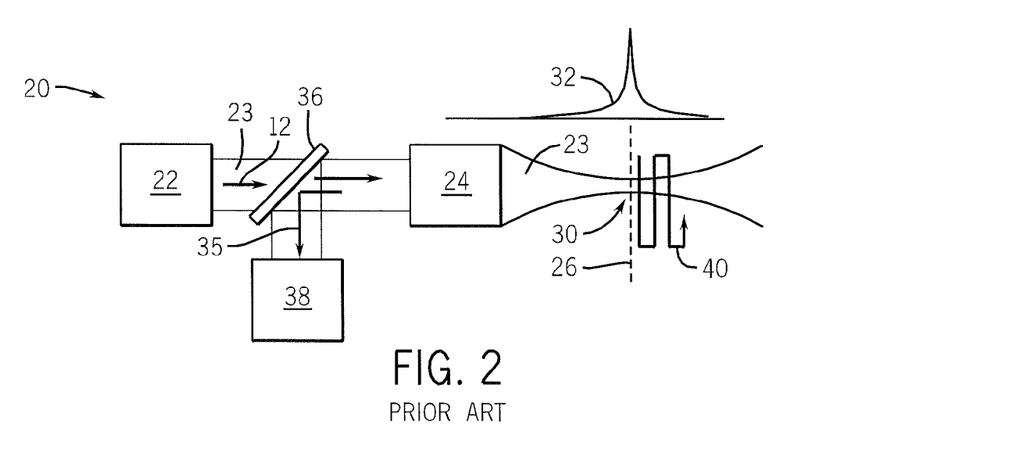
FIG. 2 is a block diagram of an existing multi-photon fluoroscopy microscope showing the optical path of light through tissue as aligned with a plot of mulitiphoton fluorescence versus distance along the optical axis.

Referring to FIG. 2, a multi-photon microscope 20, exploiting this principal, typically employs a light source 22 and provides an excitation beam 23 of stimulating photons 12 which are then received by an optical assembly 24 which focuses the beam 23 at a focal plane 26 to a focal spot 30. As the beam 12 narrows with focusing, the intensity increases and the amount of multi-photon fluorescence 32 increases rapidly causing the tissue to fluoresce principally only at the focal spot 30 in the focal plane 26. Light 35 from that fluorescence passes backward through the optical assembly 24 and is reflected off a dichroic mirror 36 separating it from an excitation beam 23 to be received by a photodetector 38. The spot 30 is scanned through tissue in a three-dimensional raster pattern 40, and brightness values obtained by the photodetector 38 are mapped to the locations in the tissue to provide the ability to reconstruct images of embedded structures in the tissue free from the influence of underlying or overlying tissue.

Such multi-photon fluorescence techniques have been used to provide sharp images of in vivo tissue up to a depth of about 600 μm. Beyond this depth, the ability to provide a small focal spot 30 (which ultimately determines the resolution of the image) degrades because of inhomogeneities in the optical properties of the intervening tissue, principally refractive index, which distort the incident waveform preventing sharp focus.

The principles of adaptive optics have been applied to correct the problem of wavefront distortion. Here the goal is to pre-distort the wavefront of the excitation beam to exactly offset the aberration caused by the intervening tissue. Such approaches may use deformable mirrors which have a continuous surface electrically flexed to change local elevation of the surface and thereby advance or retard a wavefront reflected from that surface, by precise amounts. Alternative approaches use liquid crystal devices (LCDs) which change an index of refraction as a function of voltage over their surface, for example, by using LCDs as Fresnel lenses.

Such LCD devices are relatively slow with low contrast and power handling capabilities while deformable mirrors are extremely costly and/or of relatively low resolution. The amount of phase shift achievable in a deformable mirror is severely limited by the small deformation range and the constraints imposed by a continuous mirror surface. Limitations in phase shift range prevent such devices from producing the significant phase shifts necessary to accommodate phase distortions incident to imaging structure deep within tissue. For the deformable mirror, the deflection range is smaller for higher resolution devices, effecting an undesired trade-off between the imaging depth and resolution.

BRIEF SUMMARY OF THE INVENTION

The present invention provides a phase shifting element that works not by changing the optical path length of portions of the light beam but rather by blocking portions of the light beam to produce diffractive phase shifting. Using this approach, the amount of phase shift is essentially unlimited. In one embodiment, a micro-mirror array intended for spatial intensity modulation for television and the like is used, providing an inexpensive source of high resolution, phase shifting devices.

Specifically then, the present invention provides an optical system having a light source for producing a beam of light and a micro-mirror array for receiving the beam of light shifting the phase of the beam by different amounts in different portions of the cross-section of the beam according to a control signal. An optical system focuses the beam of light into a spot within light transmissive tissue of varying optical properties. A control system, communicating with the micro-mirror array, controls the shifting of the phase of the beam to correct for the varying optical properties of the light transmissive tissue. The micro-mirror array is an electrically controlled multi-mirror diffractive element shifting the phase of the beam by constructive and destructive interference.

It is thus a feature of one embodiment of the invention to provide an improved mechanism for controlling the phase shift and thus wavefront of a light beam in a system that must transmit light through transparent but in homogenous tissue. It is another feature of the invention to provide a mechanism that may produce an arbitrary amount of corrective phase shifting required to correct for such tissue aberration, not limited by actuator range or the index of refraction of electrically active materials. It is another feature of the invention to provide for an optical system that may handle large amounts of optical power to be suitable not only for microscopy but also for laser surgery and the like. The micro-mirror array presents a readily available spatial intensity modulator widely used in the television industry for spatial phase modulation.

The light source may have a wavelength to promote multi-photon fluorescence of the light transmissive tissue at the spot.

It is thus another feature of one embodiment of the invention to provide a system for improved multi-photon fluorescence microscopy of deep structures.

The system may further include a light sensor receiving light reflected from the light transmissive tissue at the spot and wherein the control system dynamically controls the phase shifter to maximize light reflected from the spot.

It is thus a feature of one embodiment of the invention to provide a simple method of wavefront correction in an unknown biological material The light source may be an infrared source.

It is thus another feature of one embodiment of the invention to provide a phase shifter that may work over a range of frequencies including infrared frequencies.

The light source may be a laser and the invention may further include resizing optics matching the beam to the area of the phase shifter.

It is thus another feature of one embodiment of the invention to match a large area spatial modulator to the small cross-sectional area of the wavefront of a laser beam.

The diffraction pattern created by the phase modulator may be calculated from the interference of an undiffracted wavefront and a hypothetical wavefront emanating from the focal spot and passing through the light transmissive tissue of varying optical properties from the focal spot to the phase modulator.

It is thus another feature of one embodiment of the invention to provide a simple method of calculating the necessary diffraction pattern for diffractive phase shifting.

The control system may control multiple elements of the phase shifter in tandem according to Zernike coefficients.

It is thus a feature of one embodiment of the invention to limit the amount of iteration necessary to determine the necessary diffraction pattern for an unknown transition medium by modifying groups of diffraction elements according to their contribution to common types of aberration.

The control system may iteratively select multiple elements of the phase shifter to maximize the brightness of the reflected light.

It is thus another feature of one embodiment of the invention to allow correction of an unknown optical transmission medium simply by observing the intensity of reflected light.

The control system may select multiple elements of the phase shifter to vary iteratively based on the setting of the multiple elements at a previous focal spot of less depth in the light transmissive tissue.

It is thus another feature of one embodiment of the invention to provide a method of reducing the necessary iteration by employing progressive measurements deeper into the optical medium.

The light source may include different frequency sources individually activated by the control system and the control system may store a set of diffraction patterns to switch among these diffraction patterns as different light sources are enabled.

It is thus another feature of one embodiment of the invention to enable a multispectral multi-photon fluorescence microscope.

The device may further include a wavefront sensor for sensing reflected light and the phase of the reflected light over a variety of paths and the control system may correct the phase shifter according to the signal from the wave front sensor.

It is thus another feature of one embodiment of the invention to limit or eliminate the need for iteration in the phase shifter by wavefront analysis.

The phase corrector may be positioned before the optical system and the optical system may receive the beam from the phase corrector.

It is thus another feature of one embodiment of the invention to provide a system that may be easily added to existing multi-photon microscopes or other optical instruments without modification of the instruments.

The scanning microscope may be a confocal microscope.

It is another feature of one embodiment of the invention to provide the benefit of wavefront correction to conventional confocal microscopy.

These particular features and advantages may apply to only some embodiments falling within the claims and thus do not define the scope of the invention.

DETAILED DESCRIPTION OF THE INVENTION

Figure 3:
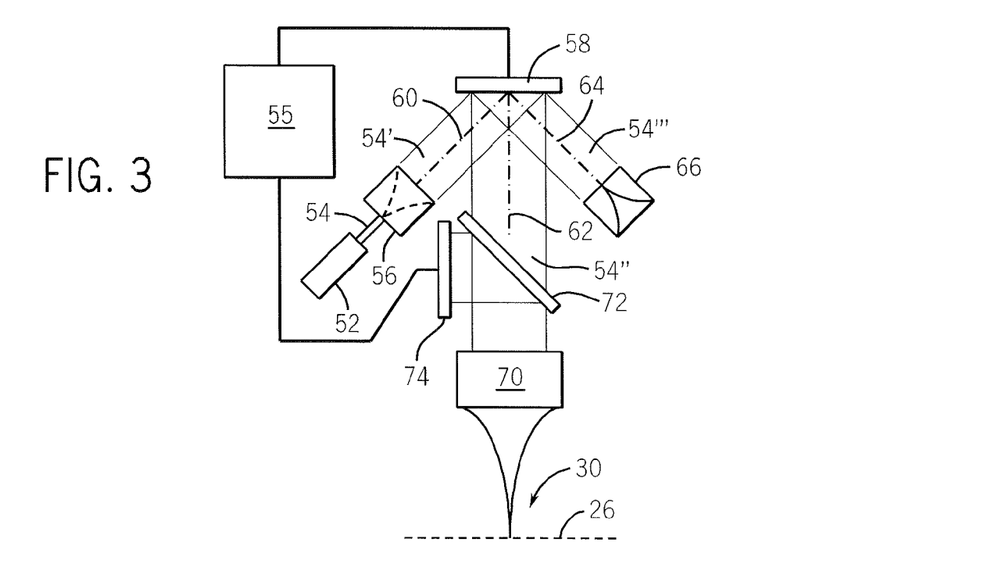
FIG. 3 is block diagram similar to that of FIG. 2 showing a multi-photon fluoroscopy microscope of the present invention employing a diffractive phase shifter.

Referring now to FIG. 3, a wavefront correction system of the present invention may be used to produce a scanning microscope 50 having a laser light source 52 directing a beam 54 toward a beam expander 56. The beam expander 56 increases the area of the beam 54 to enlarged beam 54' sized generally to direct the light along axis 60 to illuminate an active area of a controllable reflection/diffraction element 58 angled with respect to axis 60 to reflect light along axis 62.

The controllable multizone diffraction element may, for example, be a micro-mirror array such as uses the Digital Light Processing (DLP) technology of Texas Instruments of Dallas, Tex. Importantly, the controllable multizone diffraction element may controllably create multi-region diffraction zones at which light is selectively blocked or transmitted.

Figure 4:
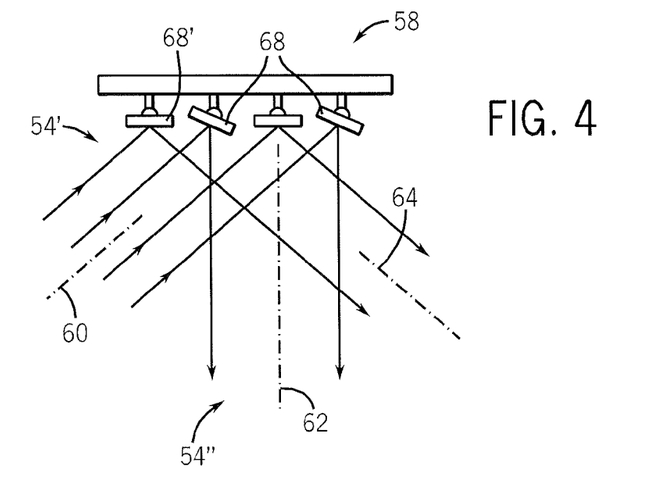
FIG. 4 is a fragmentary side elevational view of a micro-mirror array implementing the diffractive phase shifter showing the mirrors in both a first and second state for switching individual rays of an excitation beam.

Referring also to FIG. 4, when the reflection/diffraction element 58 is the DLP technology, the surface of the reflection/diffraction element 58 provides a series of micro-mirrors 68 which may be oriented in a first state (shown by micro-mirrors 68) to have their outward facing reflective surfaces tipped relative to the surface of the reflection/diffraction element 58, or in a second state 68' where their reflective surfaces are co-planar and generally parallel to with respect to the surface of the reflection/diffraction element 58. When the micro-mirrors 68 are in the first state (68), light from the beam 54 incident along axis 60 is reflected acutely along axis 62 to provide beam 54" directed to an objective lens/scanning system 70, and when the micro-mirrors 68 are in the second state (68'), the light from beam 54 incident along axis 60 is directed along axis 64 into beam stop 66 (shown in FIG. 3) where it is absorbed.

Thus beam 54' is masked by a diffraction pattern established by the position of micro-mirrors 68 and 68' which in turn can be electrically configured by a computerized control system 55. The DLP chip used for the reflection/diffraction element 58 may for example be approximately 2×1.5 cm with each micro-mirror 68 being 16 μm square and representing one pixel width in a created diffraction mask. The resolution is approximately 1024×768 providing 786,432 mirrors which may be individually controlled.

It will be understood that the beam 54' provides an intensity hologram that will exhibit multiple orders at multiple angles with respect to the surface of the reflection/diffraction element 58. The amounts of phase modulation provided by the beam 54' will generally be a function of the order. In this regard, the orientation of the micro-mirrors 68 may be used to provide a "blazed" hologram accentuating a particular order of the hologram. In the blazed hologram, the micro-mirrors 68 are oriented to reflect the light beam in a direction that coincides with the angle of the desired order, the latter being a function of the mirror spacing and the wavelength of light. The production of a blazed hologram allows the use of higher hologram orders providing increased phase modulation.

Beam 54", as diffractively modulated, is received by the objective lens/scanning system 70 which focuses the beam 54 to a focal spot 30 in focal plane 26. Reflection/diffraction element 58 is positioned at a conjugate plane of the objective lens/scanning system 70, and because it may be placed on the back side of the objective lens/scanning system 70 may be readily retrofit to a number of existing multi-photon microscopes providing the objective lens/scanning system 70.

The focal plane 26 may be scanned in depth and the focal spot scanned in two dimensions within the focal plane 26, by known optical or mechanical means, to provide for a three dimensional scanning of the focal spot 30 within the tissue. At each location of the focal spot 30, light fluorescing from the focal spot 30 may pass back through the objective lens/scanning system 70 along axis 62 to be received by a dichroic mirror 72 passing light of the frequency of beam 54' and diverting only light fluorescently generated by the tissue at the focal spot 30 to a photodetector 74.

A computerized control system 55 executing a stored program may control the reflection/diffraction element 58 based on signals from the photodetector 74 as will be described below.

Figure 5A:
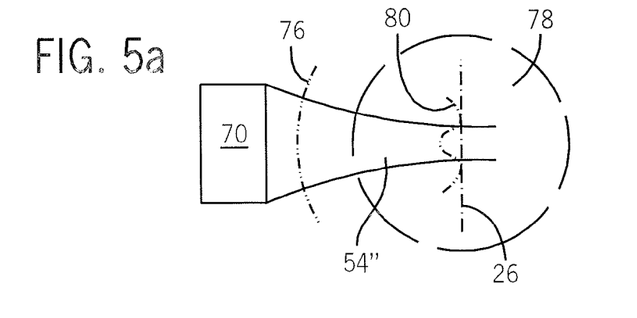
FIG. 5a and FIG. 5b are simplified representations of an excitation light beam directed into biological tissue showing in FIG. 5a distortion of the wavefront by the varying refractive indexes of the tissue which prevents a high intensity focal spot and in 5b compensation of the waveform to produce a high intensity focal spot.
Figure 5B:
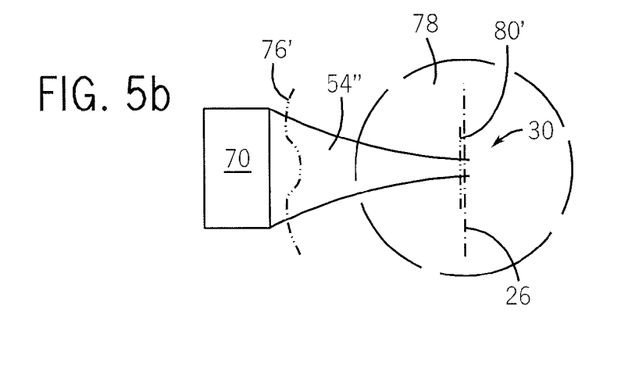

Referring now to FIGS. 3, 4 and 5*a*, when micro-mirror 68 are all set to fully reflect beam 54' to beam 54" (providing no diffraction of the beam) the objective lens/scanning system 70 will produce a wavefront 76 that, absent refractive effects of tissue 78, would produce a planar wavefront focusing at focal plane 26. Refractive effects of intervening tissue 78, however, distort the wavefront 80 at the focal plane 26 preventing the formation of a compact focal spot 30 with high photon density sufficient to produce sufficient multi-photon fluorescence. Referring to FIG. 5*b*, in the present invention, the reflection/diffraction element 58 is operated to produce a distorted wavefront 76' that when conversely distorted by the intervening tissue 78, results in a planar wavefront 80' converging at a point at the focal plane 26 producing a high intensity at focal spot 30 of small area and suitable to establish a high resolution multi-photon fluorescent activity.

Figure 6:
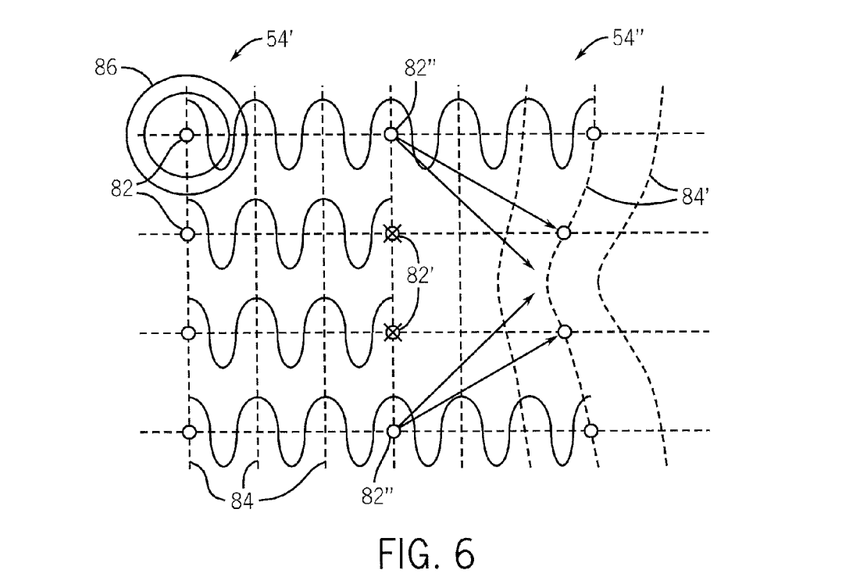
FIG. 6 is a phase diagram of the excitation light beam illustrating the Huygens-Fresnel process in which an advancing wave may be regarded as the sum of secondary waves emitted from points previously traversed by the wave and showing how blocking of emissions at some points can bend the resultant wave front.

Referring now to FIG. 6, the ability to use a spatial modulator such as the DLP to adjust the phase of a wavefront may be understood by considering the light beam 54 as a series of point emitters 82. Under the Huygens-Fresnel principle, planar wavefronts 84 may be thought of as a summation of the radially emanating wavefronts 86 from many point emitters 82 positioned along an immediately preceding wavefront. For an infinite wavefront 84 with a large number of emitters 82, it will be understood that the wavefront 84 at any point will be the vector sum of the wavefronts 86 from a given emitter 82 directly behind that point (providing a vector perpendicular to the wavefront at the point) and from the emitters 82 that symmetrically flank the given emitter 82 whose pair-wise vector summations also provide a resultant vector that remains perpendicular to the plane of the wavefront 84. Thus a planar wavefront 84 is maintained.

Referring still to FIG. 6, if some emitters 82' are subsequently blocked, for example, by the diffraction pattern of the reflection/diffraction element 58, the symmetry of the vector sums of the wavefronts 86 from emitters 82" is upset. In this case, the wavefront 84' after of the blocked emitters 82' is retarded (as shown) as a result of the longer path length from emitters 82" and distorted because of the failure of local pairwise symmetry among flanking emitters 82. The net effect is a warping of the wavefront 84' in beam 54". This diffractive effect may be used to introduce an arbitrary phase delay in any portion of the beam 54" limited only by the area of the reflection/diffraction element 58 and its resolution.

Figure 11:
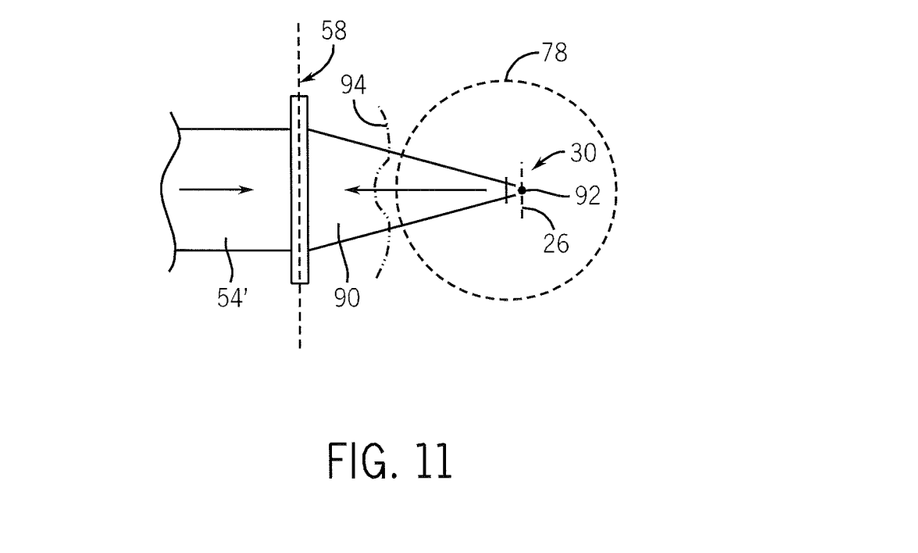
FIG. 11 is a diagram showing calculation of the arbitrary diffraction pattern when the optical properties of the traversed medium are known.

Referring now to FIG. 11, if the properties of the tissue 78 are known, the exact form of a diffraction mask implemented by reflection/diffraction element 58 may be computed by considering the interference between a planar beam 54' (unaffected by diffraction) and a beam 90 hypothetically generated by a point source 92 at the focal spot 30 having (initially) a planar wavefront distorted by the intervening tissue 78 to produce a distorted wavefront 94 interfering with beam 54' at the plane of the reflection/diffraction element 58.

Figure 7:
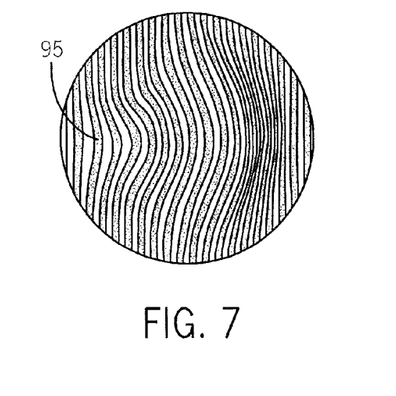
FIG. 7 is a simplified diffraction pattern that may be produced by the phase shifter of the present invention correcting for a wavefront aberration.

Referring to FIG. 7, the switching of the element in reflection/diffraction element 58 will thus produce a diffraction mask 95 having light and dark zones in rings or bands depending on the type of aberration where the black bands are areas of suppressed light and the light bands are areas of transmitted light.

If the tissue 78 is well-characterized, this calculation may be performed by the computerized control system 55 to produce the necessary driving signals for the reflection/diffraction element 58. When tissue 78 is not well-characterized, it may be approximated or its properties may be modeled and tested to produce diffraction patterns according to this general theory.

Figure 8:
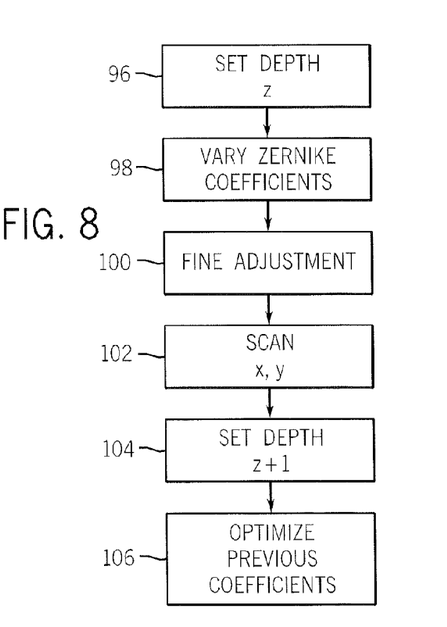
FIG. 8 is a flow chart that may be implemented by software running on the controller of FIG. 3 to determine the necessary diffraction pattern.

More typically, an iterative determination of the necessary diffraction pattern to be produced by the reflection/diffraction element 58 will be employed. Referring to FIG. 8, in an iterative approach, at process block 96, the objective lens/scanning system 70 will be set by the computerized control system 55 to "park" the focal spot 30 at a point in the tissue 78. The computerized control system 55 will then adjust the mirrors of reflection/diffraction element 58 to maximize the brightness detected by photodetector 74 such as generally indicates proper convergence of the phases of the beam 54. In one embodiment, this first measurement may be at a very shallow depth where no correction is required or very little correction is required so that optimized determination of the mirror settings may be produced quickly by well known "hill-climbing" techniques such as simulated annealing or Monte Carlo processes.

In addition or alternatively, as indicated by process block 98, various combinations of mirrors may be simultaneously iterated to reduce the solution space during the process of maximizing the reflected light and thus to reduce convergence time and the possibility of damage or photobleaching to the tissue. In the preferred embodiment, the search space is limited to an adjustment of groups of mirrors linked by Zernike polynomials. Zernike polynomials are orthogonal polynomials with simple rotational symmetry that arise in the expansion of wavefront function for an optical system with a circular pupil. Zernike coefficients corresponded various forms of aberration that are encountered in optical systems with circular pupils. Iterating through the polynomial coefficients thus provides a significantly reduced set of choices.

After the optimized Zernike polynomial coefficients are obtained, then at process block 100, optional additional fine adjustment of the mirrors may be had using conventional hill climb techniques.

At process block 102, the focal plane 26 may be scanned with these settings (making an assumption of constant aberration at a given depth) or with the Zernike coefficients held constant and fine adjustments allowed, or with a repetition of process block 98 and process block 100 at each scan point.

After the focal plane 26 is scanned, at process block 104 the focal spot may be parked at a greater depth (e.g., at a deeper focal plane 26) and this process repeated. Preferably, for each focal plane 26, the process of block 98 begins with the coefficients previously established at the preceding focal plane 26, as indicated by process block 106, further reducing the amount of iteration required.

Similarly it may be possible to pre-characterize the aberration at various points in the tissue and then to use those aberrations samples as a starter point for limited iteration on the tissue at a later time.

Figure 9:
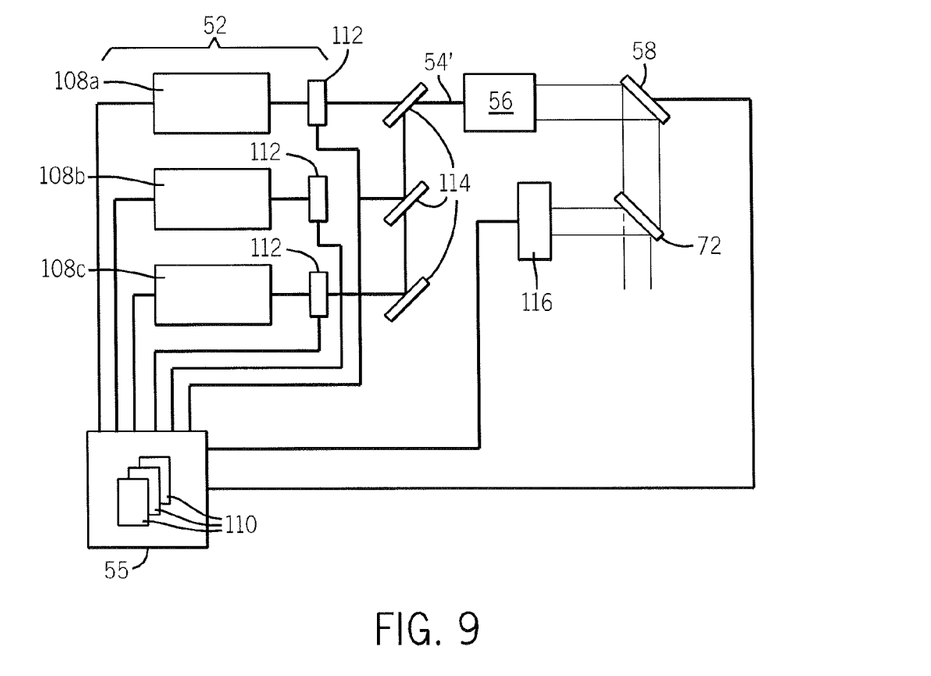
FIG. 9 is a fragmentary view of an alternative embodiment of FIG. 3 showing the use of three frequencies of light with three separate diffraction patterns and a wavefront analyzer.

Referring now to FIG. 9, the reflection/diffraction element 58, being simply a mask formed of mirrors, is not limited to operation with a given frequency of light and may be used for different light frequencies with changes in the diffraction pattern. Accordingly the light source 52 may be made up of three light sources 108*a-c* each corresponding, for example, to a different mode of fluorescent excitation.

The computerized control system 55 in this case may develop multiple diffraction patterns 110 and use those successively to control reflection/diffraction element 58 as the computerized control system 55 switches on each of the light source 108*a-c* in turn, for example, by controlling corresponding light gate elements 112. The particular beam from one light source 108*a*-108*c* may be routed to create beam 54' by means of combining mirrors and beam splitters 114.

In this embodiment or the previous embodiment, the photodetector 74 may be replaced with a wavefront detector 116, such as a Shack-Hartmann sensor detecting local tilt of the wavefront as received from the dichroic mirror 72 from the focal spot 30. The actual wavefront from the focal spot may thus be approximated by a piecewise fitting of the detected slopes of the wavefront to allow correction of the beam 54" by reflection/diffraction element 58 without iteration or with reduced iteration. This correction process uses the deduced wavefront distortion detected by the wavefront detector 116 in the calculation described with respect to FIG. 11.

Figure 10:
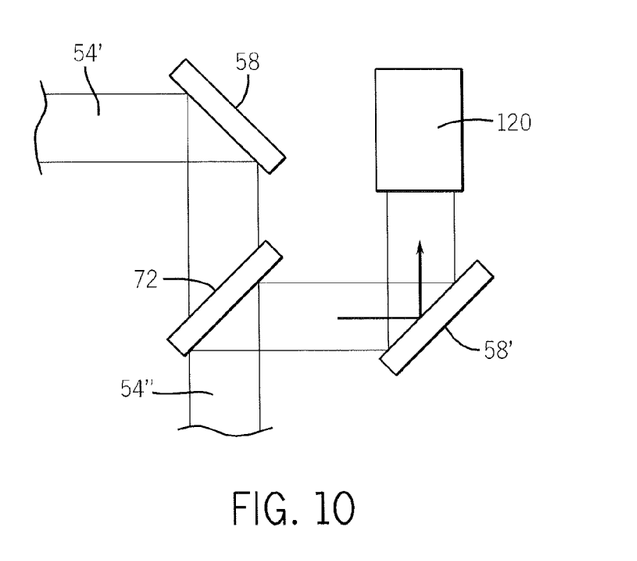
FIG. 10 is a fragmentary view of FIG. 3 or 9 showing bidirectional wavefront correction as may be used for confocal microscopy.

Referring now to FIG. 10, the present invention may also be used in a regular or confocal microscope, optionally using any of the embodiments described before, with the addition of a second reflection/diffraction element 58' providing a beam of light to a confocal analyzer 120 providing the light stop and light detector associated with a confocal microscope. The reflection/diffraction element 58' provides the conjugate wavefront modification provided by the reflection/diffraction element 58 to correct the wavefront exiting the tissue 78. In this way, wavefront aberration is corrected not only in the beam 54" going to the focal spot but also in the beam returning from the focal spot and being processed by a stop in the confocal analyzer 120.

Figure 12:
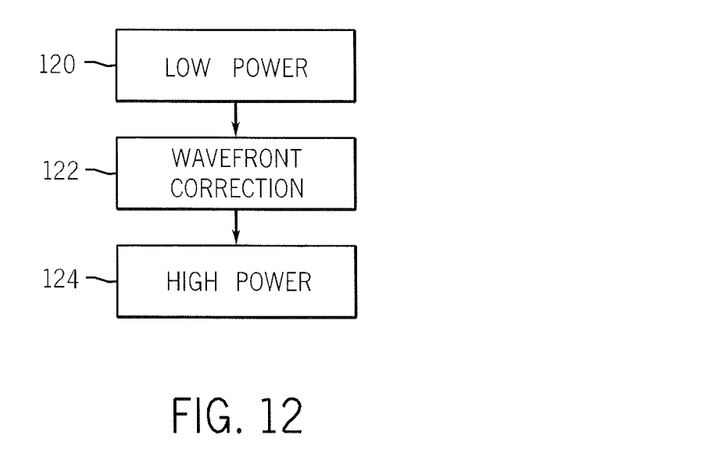
FIG. 12 is a flowchart showing operation of the invention for laser surgery where a low intensity beam is used for pre-calculating the necessary wavefront corrections.

Referring now to FIG. 11 and FIG. 3, the same optical system described above as use in a scanning microscope may be employed for laser surgery, for example, of the retina, by employing a laser light source 52 of increased power. In this case the objective lens/scanning system 70 is used to manipulate the focal spot 30 of the laser to the desired depth and location for the surgery. As shown by process block 120, the laser light source 52 (or alternate light source not shown) may be first operated in a low-power mode illuminating the focal spot 30 without significant heating of the tissue to allow for iterative correction of the wavefront per process block 122 as was described above. When the focal spot 30 has been minimized by wavefront correction to a sufficient degree, laser light source 52 is pulsed at a high power per process block 124 to provide for surgical heating of tissue at the focal spot 30.

The present invention has been described in terms of the preferred embodiment, and it is recognized that equivalents, alternatives, and modifications, aside from those expressly stated, are possible and within the scope of the appending claims.

I claim:

1. An apparatus for the correction of tissue induced optical aberration comprising:
   a light source for producing a beam of light;
   a diffraction element for receiving the beam of light and shifting the phase of the beam by different amounts in different portions of a cross-sectional area of the beam according to a control signal by controllably creating multi-region diffraction zones at which light is selectively blocked or transmitted;
   an optical system focusing the beam of light to a focal spot within light transmissive tissue of varying optical properties;
   a sensor providing an indication of tissue induced aberration;
   a control system communicating with the sensor and diffraction element to control the shifting of the phase of the beam according to the computed diffraction zones to correct for the varying optical properties of the light transmissive tissue;
   wherein the diffraction element provides electrically controlled independent elements shifting the phase of the beam by blocking and transmitting the beam of light according to the diffractions zones to create constructive and destructive interference;
   wherein the control system controls multiple elements of the diffraction element in tandem groups according to Zernike coefficients.

2. An apparatus for the correction of tissue induced optical aberration comprising:
   a light source for producing a beam of light;
   a diffraction element for receiving the beam of light and shifting the phase of the beam by different amounts in different portions of a cross-sectional area of the beam according to a control signal by controllably creating multi-region diffraction zones at which light is selectively blocked or transmitted;
   an optical system focusing the beam of light to a focal spot within light transmissive tissue of varying optical properties;
   a sensor providing an indication of tissue induced aberration;
   a control system communicating with the sensor and diffraction element to control the shifting of the phase of the beam according to the computed diffraction zones to correct for the varying optical properties of the light transmissive tissue;
   wherein the diffraction element provides electrically controlled independent elements shifting the phase of the beam by blocking and transmitting the beam of light according to the diffractions zones to create constructive and destructive interference;
   wherein the control system varies multiple elements of the diffraction element based on settings for the multiple elements selected for a previous focal spot of lesser depth in the light transmissive tissue.

3. An apparatus for the correction of tissue induced optical aberration comprising:
   a light source for producing a beam of light;
   a diffraction element for receiving the beam of light and shifting the phase of the beam by different amounts in different portions of a cross-sectional area of the beam according to a control signal by controllably creating multi-region diffraction zones at which light is selectively blocked or transmitted;
   an optical system focusing the beam of light to a focal spot within light transmissive tissue of varying optical properties;
   a sensor providing an indication of tissue induced aberration;
   a control system communicating with the sensor and diffraction element to control the shifting of the phase of the beam according to the computed diffraction zones to correct for the varying optical properties of the light transmissive tissue;
   wherein the diffraction element provides electrically controlled independent elements shifting the phase of the beam by blocking and transmitting the beam of light according to the diffractions zones to create constructive and destructive interference;
   wherein a light source includes multiple wavelength sources individually activated by the control system and wherein the control system stores a set of multi-region diffraction zones to switch among these multi-region diffraction zones as different wavelength sources are enabled.

* * * * *